United States Patent [19]

Hetherington

[11] Patent Number: Plant 6,830

[45] Date of Patent: Jun. 6, 1989

[54] ORCHID LAELIOCATTLEYA BALLET FOLKLORICO 'ELOQUENCE'

[75] Inventor: Ernest E. Hetherington, Arcadia, Calif.

[73] Assignee: Stewart Orchids, Carpinteria, Calif.

[21] Appl. No.: 15,371

[22] Filed: Feb. 17, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Howard A. Kenyon

[57] ABSTRACT

A new and distinct variety of orchid, more particularly a Laeliocattleya hybrid plant having flowers of large size and clear coloring with flowers erectly carried on strong sprays. The new variety is distinct from siblings of its grex by its outstanding vigorous plant structure as well as frequency and freedom of bloom. Of primary note with this cultivar is its freedom from disease and tolerance to lower growing temperatures which permits it to be grown out of doors in many areas.

1 Drawing Sheet

DISCOVERY OF THE NEW VARIETY

The orchid of this application was discovered by the undersigned discoverer as an outstanding member of a large sibling population of the hybrid Laeliocattleya - Ballet Folklorico (herein abbreviated as Lc. Ballet Folklorico). In 1970 Lc. Ballet Folklorico had been developed in the orchid nursery of Fred A. Stewart, Inc. at San Gabriel, Calif. by crossing Lc. Song of Norway, clone #5270×L. Grandiflora 'Elizabeth Addy'. The Lc. Song of Norway was the pod parent (mother plant). The resultant grex of Lc. Ballet Folklorico was registered by the Stewart Nursery with the Orchid Hybrid Registration Committee in London, England, in 1975, and published in the 1971–75 volume of Sander's Orchid Hybrid List. The new orchid was registered as "Stewart cross #1738 Lc. Ballet Folklorico".

In May, 1975, the new variety appeared as a single outstanding plant among a large population of siblings of Lc. Ballet Folklorico, all cultivated and blooming at Stewart's San Gabriel nursery. The plant of the new variety was immediately recognizable as superior in its flowering and general growth habit to all other members of the large population of the hybrid group Lc. Ballet Folklorico. After the new variety had been observed for a period of time, its other features of superior growth and structure were also noted.

ASEXUAL REPRODUCTION

After its discovery in August 1975, the original plant was placed in the laboratories of the Fred A. Stewart, Inc. nursery. During the years since 1975, a large number of plants of the new cultivar have been asexually produced by the meristem tissue culture process. Portions of tissue called meristems, comprised of unspecialized cells, capable of later differentiation, were cut from the plant and developed, under carefully controlled sterile conditions into new individual plants. This has been an ongoing process to cultivate this exceptional variety. The population thus produced is carried under the Code Number SM-403. All asexually propagated tissue from this cultivar carries this code number.

All of the propagations reproduced true to the original in both plant, flower and other characteristics. A substantial cross section have flowered. They are exactly the same as the mother clone, with no signs of mutation. All plants of the new variety have continued to be readily distinguishable from both parents and all other siblings of Lc. Ballet Folklorico in flower quality, plant growth habit and other characteristics. The new variety has been designated as Lc. Ballet Folklorico cultivar var. 'Eloquence'.

DESCRIPTION OF THE PHOTOGRAPHS

The upper photograph is a close-up view of a spray of flowers typical of the new variety. The lower photograph shows the same flowers but as viewed from a greater distance, so as to reveal the appearance of the plant foliage and flowers and general growth habit.

DESCRIPTION OF THE PLANT

The plant and its flowers are illustrated in the color photographs accompanying this specification. In some respects, the plant is typical of a Laeliocattleya hybrid. However, because of the rarely used Laelia grandiflora species, its growth habit and flowering are almost unique in the Cattlya hybrid complex. Its strap-like, coriacious leaves are erectly carried lanceolate. The average leaf is 25 centimeters to 32 centimeters long. They are narrower than most Laeliocattleya hybrids which is advantageous. The plant attains a growth on maturity of 32 centimeters to 41 centimeters. However, the plant develops a structure of superior and unusual strength and resiliency in all of its parts. The rhizome is short, branching often into a compact plant with many flowering leads. The growth, in addition to being compact, is naturally erect without any need to support the leaves and flower stems. The strong flower sprays are borne from the axils of the growth and are of superior strength. Its flowering habit is dependable. The flowers develop from small sheaths throughout the winter and spring season. Many plants bloom again in the summer and into the fall. The plants are exceptionally hardy in comparison with similar orchids. They have been virus and pathogen free during development, both in the original population of Lc. Balled Folklorico, in the cultivar 'Eloquence', and in the meristem population of the new variety, 'Eloquence'. The cells have an even chromosome compliment, which is indicated by the plant growth habit and ease of propagation which is indicative of uniform cytology.

DESCRIPTION OF THE FLOWER

The outstanding merit of the new variety, in addition to cold tolerance, is the size, clarity and delicacy of coloring of the flowers. The pastel colorations are in harmony with the spottings and markings of the large hips. What is especially notable is the excellent carriage of the very large flowers with each flower in perfect position on the stem — a characteristic not always found in Cattleya and Laeliocattleya hybrids.

Sepals and petals are of a delicate lavender, best identified from the British Horticultural Color Chart, as Mauvette, Vol. II, Chart Page 537, Swatch 537/3. (Close horticultural well-known examples are B.H.C.C. *Haberlea rhodopensis.*) On the tips of the petals there is a thin flare of violet purple the exact color of the lip markings. The texture of the sepals and petals is sparkling and clear. The flowers hold their color very well in comparison to others in this line of breeding. The attractive labellum is in nice balance to the sepals and petals, while the focal point of the flower are in nice harmony. The lip can best be described as large, shapely with side lobes closed well over the column. Throughout most of its portions, it is spotted and barred, Violet Purple, Vol. II, Pg. 733, Swatch 733/3. Within the throat of the labellum, there is a slight amount of yellow B.H.C.C. Pg. 5, Swatch 4/1. The shading is very subtle, however.

The flowers of the variety are larger and stronger in structure than the average grex or cultivar in this line of breeding. The flowers average 7 centimeters in petal width with a total span of 17–20 centimeters. The new variety can carry as many as 4 flowers on each spray on a mature, well-grown plant. The flowers are perfectly carried on strong erect flower spikes. The petals are flat and well carried somewhat forward in contrast to other cultivars of this grex and line of breeding. They are carried without twisting, turning and recurving. The sepals and petals are in symmetrical balance to the lip and create a good round shape to the flower as a whole. What is exceptional in this particular cultivar is the flowers last exceptionally well regardless of weather conditions or temperature, lasting 3 to 4 weeks on the average.

The blooming season is primarily winter into spring. It can vary according to cultural conditions where it is grown. What has been observed in this cultivar is temperature responsive in its flowering which makes it very valuable for forcing of pot plants. If grown outdoors, the flowering season is some weeks later than if grown in a greenhouse. The flowers have a delicate floral fragrance on the plant.

The above described characteristics of the new variety make it of exceptional value in the commercial orchid plant sales market. The exceptional vigor of this particular cultivar, excellent blooming season, total reliablity of bloom and freedom of bloom are characteristics which set this particular cultivar above not only its siblings in the grex, but other gregi in this entire line of breeding or other lines of breeding.

What is claimed is:

1. A new and distinct variety in the hybrid genus Laeliocattleya, discovered as a superior variety of the grex Lc. Ballet Folklorico, named 'Eloquence', characterized by a combination of clearness of coloring, superior flower substance, size, shape and further characterized by its exceptional vigor, reliability of bloom, cold tolerance and lasting qualities.

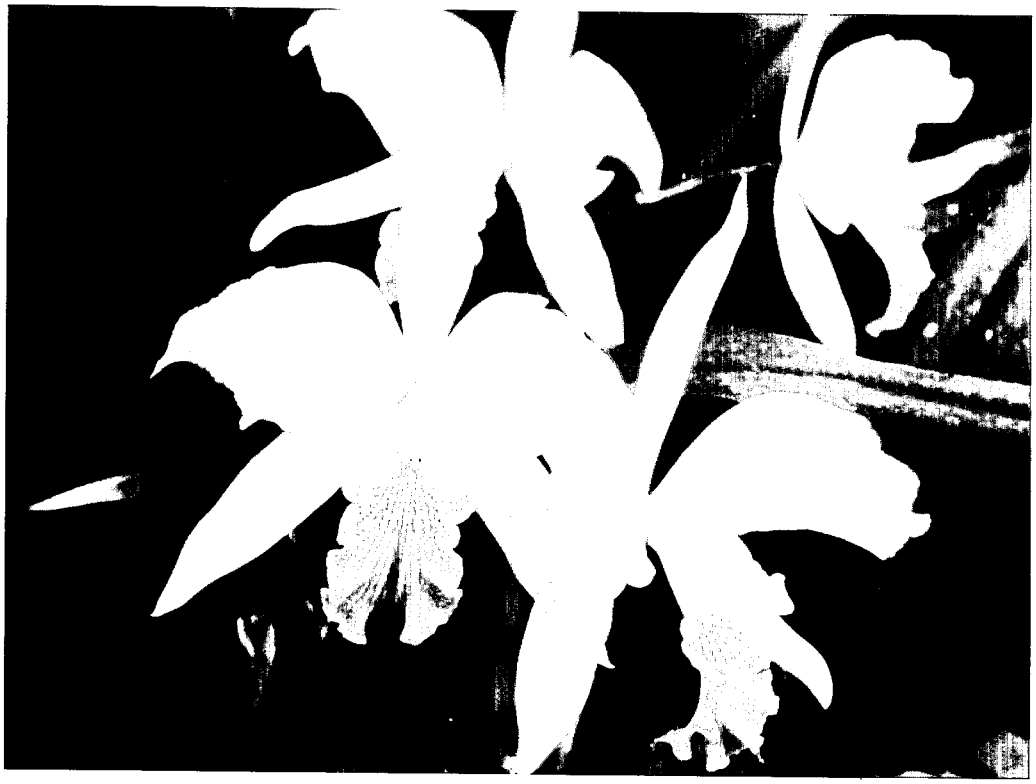
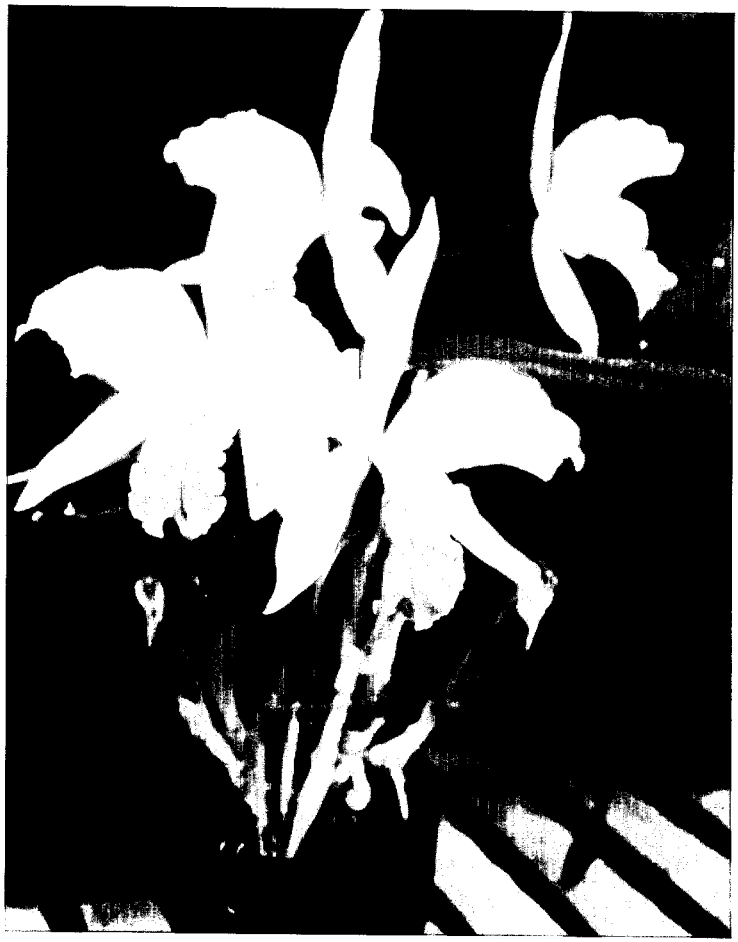

* * * * *